(12) United States Patent
Guan et al.

(10) Patent No.: US 8,890,534 B2
(45) Date of Patent: Nov. 18, 2014

(54) SURFACE IONIZATION DETECTOR

(75) Inventors: Yafeng Guan, Dalian (CN); Weiwei Li, Dalian (CN); Daoqian Zhu, Dalian (CN); Jianwei Wang, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 661 days.

(21) Appl. No.: 13/133,652

(22) PCT Filed: Nov. 5, 2009

(86) PCT No.: PCT/CN2009/074820
§ 371 (c)(1),
(2), (4) Date: Jun. 8, 2011

(87) PCT Pub. No.: WO2010/069213
PCT Pub. Date: Jun. 24, 2010

(65) Prior Publication Data
US 2011/0234235 A1   Sep. 29, 2011

(30) Foreign Application Priority Data

Dec. 19, 2008   (CN) .......................... 2008 1 0229982

(51) Int. Cl.
*G01N 27/62* (2006.01)
*G01N 30/64* (2006.01)
*H01J 49/16* (2006.01)

(52) U.S. Cl.
CPC .............. *G01N 30/64* (2013.01); *G01N 27/626* (2013.01); *H01J 49/16* (2013.01); *G01N 2030/647* (2013.01)
USPC .................... 324/468; 250/423 R; 250/423 F; 250/288; 250/282; 250/281

(58) Field of Classification Search
CPC .......... G01N 27/626; G01N 2030/647; G01N 30/64; H01J 49/16
USPC ........... 324/459–470; 250/288, 282, 281, 424
See application file for complete search history.

(56) References Cited

U.S. PATENT DOCUMENTS 5,014,009 A * 5/1991 Arimoto et al. ............... 324/468
5,310,474 A * 5/1994 Hetrick et al. ................ 204/425
(Continued)

FOREIGN PATENT DOCUMENTS

| JP | 612624256 | 11/1986 | |
|----|-----------|---------|---|
| JP | 09-210982 | * 8/1997 | ............. G01N 30/70 |
| JP | 9210982 A | 8/1997 | |
| JP | 10115606 A | 5/1998 | |

*Primary Examiner* — Tung X Nguyen
*Assistant Examiner* — Alesa Allgood
(74) *Attorney, Agent, or Firm* — Novick, Kim & Lee, PLLC; Allen Xue

(57) ABSTRACT

The present invention refers to a surface ionization detector comprises an emitter, a heating rod, a collecting electrode, a reducing liner and a housing. The emitter is made of molybdenum, platinum or alloy, and in the form of cylinder or a wire spiral. The heating rod heats and supports the metal emitter. When the heating rod is heated to 300-500° C., organic amine compounds collide with the surface of the emitter, generating positive ions through surface thermal ionization and thus are detected. The lowest detecting limit value of tertiary amine by the detector in the present invention can achieve to $10^{-14}$ g/s. The response to other hydrocarbons, ketones, etc., is 5-6 orders of magnitude lower than that of organic amines. The detector can selectively detect amines, hydrazines and their derivatives, and so on. The detector can be used as a detector for a gas chromatography system adopting capillary column or packed column, or alternatively be used alone as a sensor.

13 Claims, 4 Drawing Sheets

(56) References Cited

U.S. PATENT DOCUMENTS

| | | | |
|---|---|---|---|
| 5,866,004 A | * | 2/1999 | Houck et al. ............... 210/634 |
| 6,855,557 B2 | * | 2/2005 | Kishkovich et al. .......... 436/106 |
| 7,352,187 B2 | * | 4/2008 | Knapp et al. ................. 324/460 |
| 7,750,654 B2 | * | 7/2010 | Okumura et al. ........ 324/750.08 |

\* cited by examiner

SURFACE IONIZATION DETECTOR

CROSS-REFERENCES TO RELATED APPLICATIONS

The present application claims the benefit of the Chinese Patent Application No. 200810229982.6, filed Dec. 19, 2008, which are incorporated herein by reference in its entirety and for all purposes.

THE TECHNICAL FIELD

The present invention relates to a surface ionization detector (SID). The SID can be used for the detection of organic amines and hydrazines. It could be coupled with a capillary tube or packed column gas chromatograph, or alternatively be used alone as a sensor.

BACKGROUND

Amines and heterocyclic amines are widely used in various industries, including chemical industry, pharmaceutical industry, and so on. They are present in waste waters drained by industrial factories, farms, drug manufacturing enterprises, food producing enterprises, and so on. Low concentrations of amines are poisonous to humans and animals. Because all the above samples contain higher concentrations of other co-existing organic compounds, detecting the concentration of amines selectively, rapidly, and sensitively is important for environmental protection, industry monitoring and food quality assurance.

For the detection of nitrogen-containing compounds, the nitrogen-phosphorus detector (NPD) or thermal-ionization detector (TID) is the most sensitive detector at present. But the NPD/TID responds to almost all types of nitrogen-containing compounds and cannot respond selectively to amines. Moreover, the NPD/TID is not very sensitive to tertiary amines, secondary amines, and heterocyclic amines. Its minimum detectable amount towards those amines is only about $10^{-10}$ g, and the repeatability is not very good. Besides, hydrogen is necessary as the burning gas when the NPD works, which is a potential safety risk.

The principle of the surface ionization detector (SID) is surface ionization. Molecular beam or atoms (or molecules) in the vapor collides with a hot solid surface, and parts of atoms (or molecules) are ionized into positive or negative ions when they are thermally desorbed from the solid surface, as shown in FIG. 1.

For some positive ion produced by ionization, wherein $$N = N_0 + N_\pm; \quad \alpha_+ = \frac{N_+}{N_0} = \frac{g_+}{g_0}\exp\left(\frac{\Phi - IP}{kT}\right) = A\exp\left(\frac{\Phi - IP}{kT}\right) \quad (1)$$

$N_+$ is the number of the thermally desorbed positive ion per unit area and unit time;

$N_0$ is the number of the thermally desorbed neutral atom (or molecule) per unit area and unit time;

$\Phi$ is the work function of the metal; if the metal is oxidized, $\Phi$ increases;

IP is the ionization energy of the atom or molecule;

$g_+$ and $g_0$ are the statistical weight factor of the positive ion and that of the neutral atom or molecule, respectively;

k is the Boltzmann constant;

T is the surface temperature of the metal emitter.

Compounds that can be surface ionized include: 1) IA group metal atoms with low ionization energies, such as sodium, potassium, strontium atom, and so on; 2) oxides of transition metals, rare-earth metals and uranium, inorganic compounds containing sulfur or halogens; 3) organic compounds containing nitrogen or oxygen, such as triethylamine, trimethylhydrazine, aniline, phenols, some amino acids, acetic acid, formic acid, and so on. Among the organic compounds, the surface ionization efficiencies of amines, hydrazines and their derivatives are very high. The ionization efficiency of tertiary amines even reaches 0.2~0.5. Studies of mass spectrometry show that the types of the ions produced by surface ionization of organic amines are very few, mainly including $(M-H)^+$, $(M-Alk)^+$, $(M+H)^+$, $(M-H-2nH)^+$, $(M-Alk-2nH)^+$, and so on. On collision with hot metal surfaces, most organic compounds first dissociate into radicals with low ionization energies and are then surface ionized. Assuming an organic compound dissociates into radicals s, r, p, q, and so on. For a radical s, $$i_s(T) = enY_s(T) \cdot \beta_s(T) \quad (2)$$

n is the total number of the organic compound colliding with the metal surface;

e is the electron charge in an electron;

T is the surface temperature of the metal emitter;

$Y_s(T)$ is the yield of the organic compound dissociating into radical s;

$\beta_s(T)$ is the ionization efficiency of radical s. According to equation (1), $$\beta_s(T) = \frac{\alpha_s}{1+\alpha_s} = \frac{1}{1 + A_s^{-1}\exp\left(\frac{IP_s - \Phi}{KT}\right)} \quad (3)$$

Supposing the produced total current is $I_{total}$, $$I_{total} = i_s(T) + i_p(T) + i_q(T) + i_r(T) = en(Y_s(T) \cdot \beta_s(T) + Y_p(T) \cdot \beta_p(T) + Y_q(T) \cdot \beta_q(T) + Y_r(T) \cdot \beta_r(T)) \quad (4)$$

According to equation (4), for an organic compound that happens to be surface ionized, values of $Y_s(T)$, $Y_p(T)$, $Y_q(T)$, $Y_r(T)$, $\beta_s(T)$, $\beta_p(T)$, $\beta_q(T)$, and $\beta_r(T)$ are constants once the structure of detector, the surface temperature of the metal emitter, the electrical field strength, the makeup gas flow, etc. are fixed. Thus the total current produced by surface ionization is proportional to the mole amount of the organic compound. It is the theoretical basis for quantitatively determination of organic compounds by SID.

Usually, $\Phi - IP < 0$. According to equation (2) and (3), the higher the work function $\Phi$ and the temperature are, the higher the ionization efficiency is. In order to improve the ionization efficiency, metals with high work functions should be used as the emitter, such as platinum, iridium, molybdenum, and so on. Besides, metal surfaces should be probably oxidized in order to increase the work function; and metals should be heated to stay at a high surface temperature.

According to equation (2) and (3), the surface ionization efficiency $\beta$ is relative to the ionization energy $\Phi$ of the organic compound. The smaller the ionization energy is, the more easily surface is ionized. If the difference in ionization energies of two compounds is 1 eV, their ionization efficiencies can differ maximally by $10^5$ times. Among the organic compounds, amines, hydrazines and their derivatives with the lowest ionization energies are the most easily to be surface ionized. Therefore, the SID can detect them with high selectivity.

Shimadzu Corporation developed the commercialized SID in 1986 (Patent No.: CN86103355, JP61264256, EP26223, WO8606836, U.S. Pat. No. 5,014,009, DE3686162). The detector can detect amines selectively. Its response to tertiary amines is $10^5$~$10^6$ times higher than that to ketones. It has almost no responds to hydrocarbons; and its selectivity is very high. To tertiary amines, the sensitivity of the SID is 10~100 times higher than that of the NPD. To secondary amines and primary amines, the sensitivity of the SID is not as high as that of the NPD, but higher than that of the flame ionization detector (FID). The SID only requires the carrier and the makeup gas, and hydrogen is not necessary. Its operations are simple, and the use is safe.

However, there are some disadvantages in the SID commercialized by Shimadzu as in the following: 1) The electrical current is directly applied on the coiled platinum wire to heat it. Thus there must be enough space between adjacent wire loops to guarantee insulation. Moreover, the coiled platinum wire works also as the emitter, therefore, the surface area of the emitter is relatively small, and the sensitivity is not high. 2) Only the nozzle part is kept hot, and most of the metal housing and the stainless steel collecting electrode are located in a place with relatively low temperatures. Since the alkalinity of amines is relatively high, they are apt to be adsorbed by metals, causing significant peak tailing, and cannot detect tertiary amines of less than $10^{-11}$ g/s.

Therefore, if the adsorption of amines by metal materials in the detector is maximally reduced or avoided, SID can detect tertiary amines of less than $10^{-12}$ g/s, which will be one of the most sensitive and selective detectors to amines and hydrazines.

SUMMARY OF INVENTION

The object of the present invention is to provide a surface ionization detector (SID), wherein the metal emitter of the detector is heated indirectly, providing it relatively large surface area, resulting in high sensitivity. Meanwhile, a quartz (or glass) flared reducing liner and a quartz heating rod are used in the detector, keeping the whole detector hot, reducing the adsorption of amines to the greatest degree. The minimum detectable amount (MDA) of tertiary amines reaches $1\times10^{-14}$ g, which is 2~4 orders of magnitude smaller than that of the SID commercialized by Shimadzu. The response of the detector to tertiary amines is $10^5$~$10^6$ times higher than that to ketones, showing rather high selectivity. Meanwhile, the detector only needs the carrier gas and the makeup gas, the operations are relatively simple. Coupled with suitable sample pretreatment techniques, GC-SID can be widely used to detect nitrogen-containing drugs in complex samples such as urine, blood, etc, nitrogen-containing pesticides in foods, narcotics, and so on.

In order to accomplish the above objective, the present invention provides a technical scheme as follows:

A SID comprises a metal emitter, a heating rod, a collecting electrode, a reducing liner, a housing, and so on.

The metal emitter is placed at the outer wall of the heating rod. The collecting electrode is cylindrical, and its lower part is placed in the liner. The liner is placed in a housing. The bottom of the housing is open. The emitter, the heating rod, the collecting electrode, and the liner are kept coaxial. The collecting electrode is electrically connected with an external micro-current amplifier by a lead passing through the housing.

The metal emitter can be made of molybdenum, platinum, iridium, rhodium or their alloys; usually, relatively cheap molybdenum or platinum are adopted. The shape of the metal emitter can be cylindrical or a wire spiral. If it is cylindrical, the surface of the cylinder can be thinly grooved into screw thread or gridding to increase the surface area. A polarization voltage of +50~400 V is directly applied on the metal emitter without the need of another separate polarization electrode. A weak positive electric field is formed between the metal emitter and the collecting electrode to collect the positive ions produced by the ionization of samples on the metal emitter surface.

The heating rod, whose shell is made of quartz to avoid the adsorption of organic amines, heats and supports the metal emitter.

The collecting electrode, which is made of conductive materials, is used to capture positive ions signals produced by ionization on the metal emitter surface.

The outer diameter of the heating rod is 0.8~5 mm, the inner diameter of the collecting electrode is 1~2 mm bigger than the outer diameter of the heating rod. In this case, the detection cell is less than 600 μL, which can be used as a detector for capillary column or packed column gas chromatograph.

The lower end of the reducing liner is a conduit with a reducing inner diameter, guiding the gas flow and preventing the back diffusion of samples. The reducing liner is made of inert quartz or glass after inert surface treatment to avoid the adsorption of amines. The inner diameter of the upper end of the reducing liner is 0.1~1 mm larger than the outer diameter of the lower end of the collecting electrode, muff-coupled with the collecting electrode. The diameter of the inner orifice in the lower end of the liner ranges from 0.5~2 mm, with a length of 10~40 mm, where a capillary column can be inserted and remains a certain space in between for the makeup gas to flow into the liner.

The bottom of the housing is open, which has an adapter for packed column or capillary column. The adapter for capillary column has a capillary in its center.

The housing is placed in a heated region. During operation, the whole detector is kept at a setting temperature (150~400° C.). Consequently, the temperature of the collecting electrode is close to the setting temperature of the detector, reducing the adsorption of amines dramatically.

Compared with the SID commercialized by Shimadzu, the present invention has the following advantages:

1) The emitter can be in the form of cylinder or wire spiral. If it is in the form of cylinder, the surface of cylinder can be thinly grooved into screw thread or gridding to increase the surface area. The surface area of the metal emitter is relatively large, leading to the high sensitivity of the detector.

2) Polarization voltage is applied directly on the metal emitter without the need of an additional polarization electrode, resulting in a simple structure.

3) The outside shell of the heating rod is made up of quartz, which is high-temperature resistant and chemically inert; the adsorption of amines is very small.

4) The quartz (or glass) reducing liner is designed to be flared; it can guide the flow of the make-up gas and the carrier gas. It is made of inert quartz or glass, and the adsorption of amines is rather small.

5) The whole detector housing is placed in a heated zone. The whole detector is kept hot, keeping the temperature of the collector close to that of the detector, reducing adsorption of amines.

6) A capillary column or a packed column can be inserted directly into the detector without the need of a nozzle, reducing extra-column peak broadening of the sample.

The detector in the present invention successfully solves the problem of adsorption of trace amines. The MDA to tertiary amines is $1\times10^{-14}$ g/s, which is 2~4 orders of magnitudes smaller than that of SID commercialized by Shimadzu.

DESCRIPTIONS OF DRAWINGS

Figure 1:
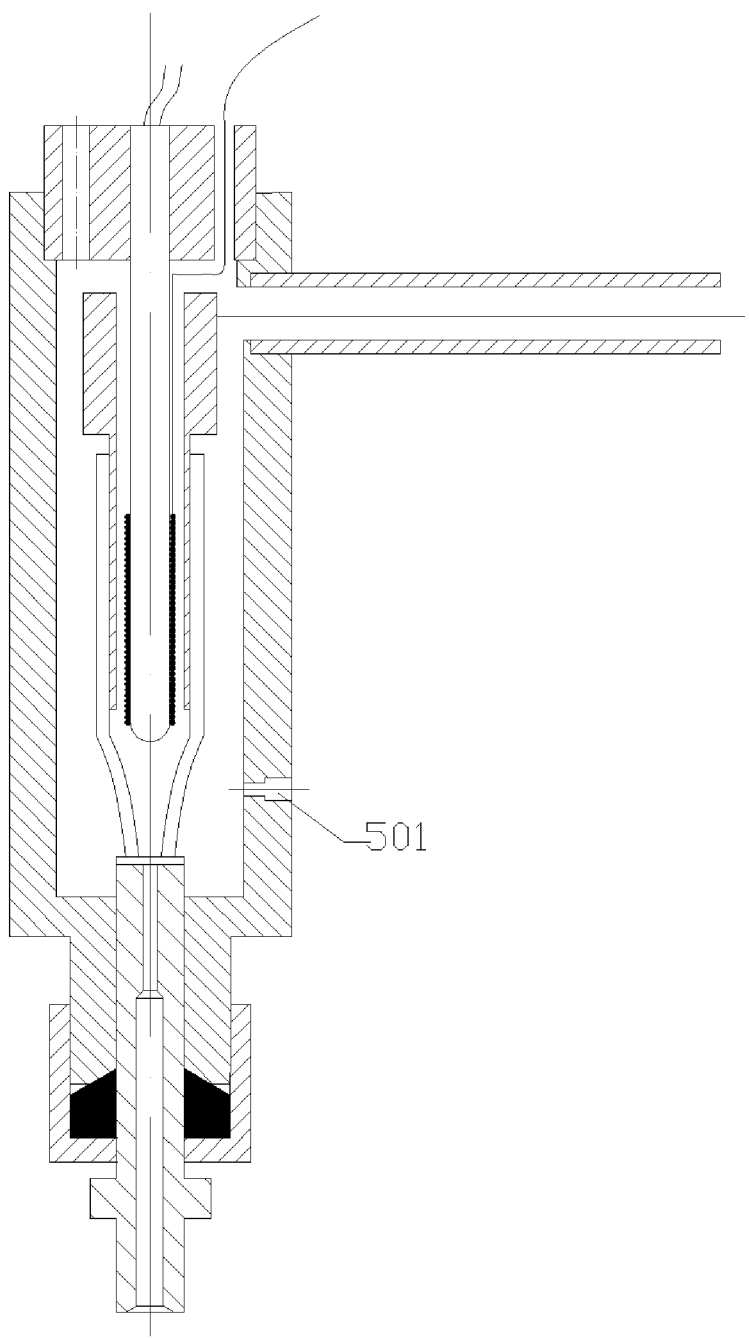
FIG. 1 is a schematic illustration of the SID and its heating block in the present invention, wherein a makeup gas pipe is welded into 501.
Figure 2:
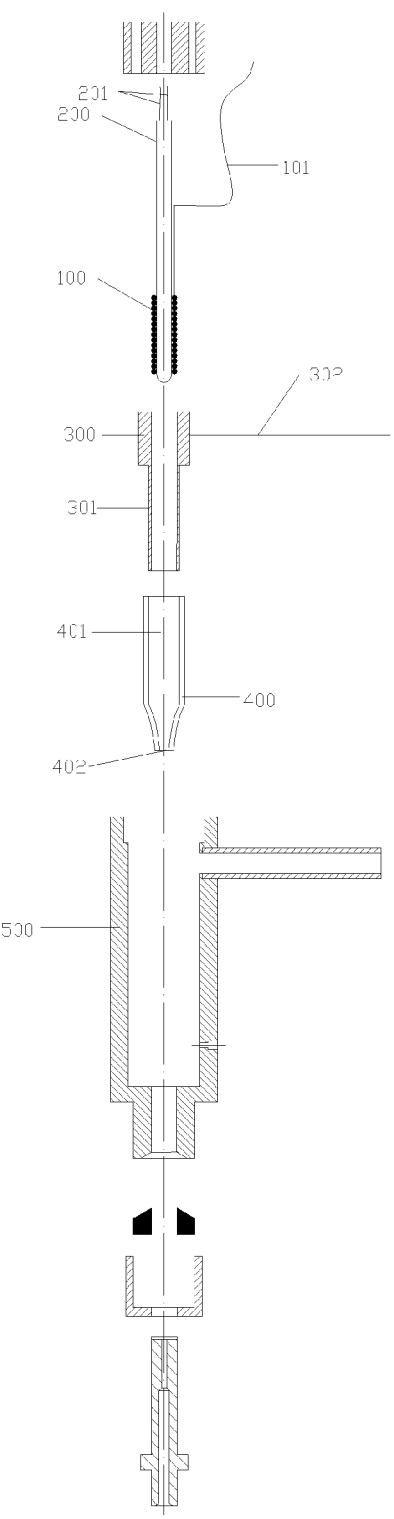
FIG. 2 illustrates structures of discrete parts of the SID in the present invention. 100—metal emitter, 101—lead, 200—heating rod, 201—heating filament in the heating rod; 300—collecting electrode, 301—lower part of the collecting electrode, 302—lead for the collecting electrode, 400—reducing liner, 401—upper part of the reducing liner, 402—lower part of the reducing liner; 500—housing.
Figure 3:
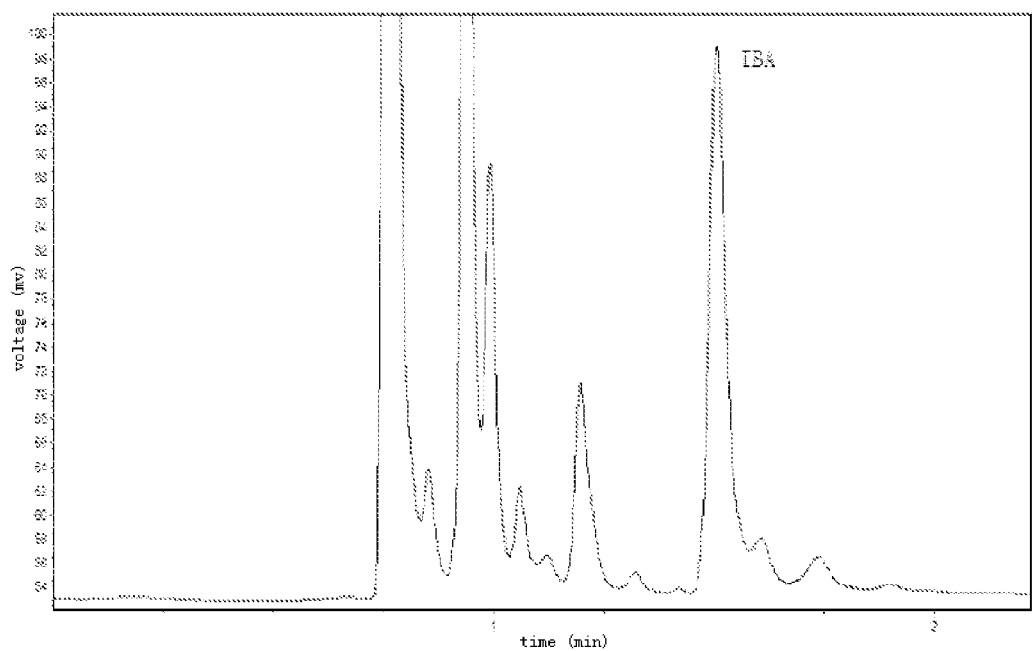

FIG. 3 is the chromatogram of 0.1 μL 20 μg/L tributylamine/acetone (2 pg TBA) obtained by a gas chromatograph coupled with the SID in the present invention. Experimental conditions: the detector temperature is 270° C., the Mo wire temperature is 370-380° C.; 150 mL/min of air supplies as the makeup gas; the injector temperature is 260° C.; the oven temperature is isothermally 140° C.; the chromatographic column is 30 mm×0.53 mm i.d.×1 μm SE54 column; 8 mL/min of nitrogen in the constant mode supplies as the carrier gas; splitless injection is used.

Figure 4:
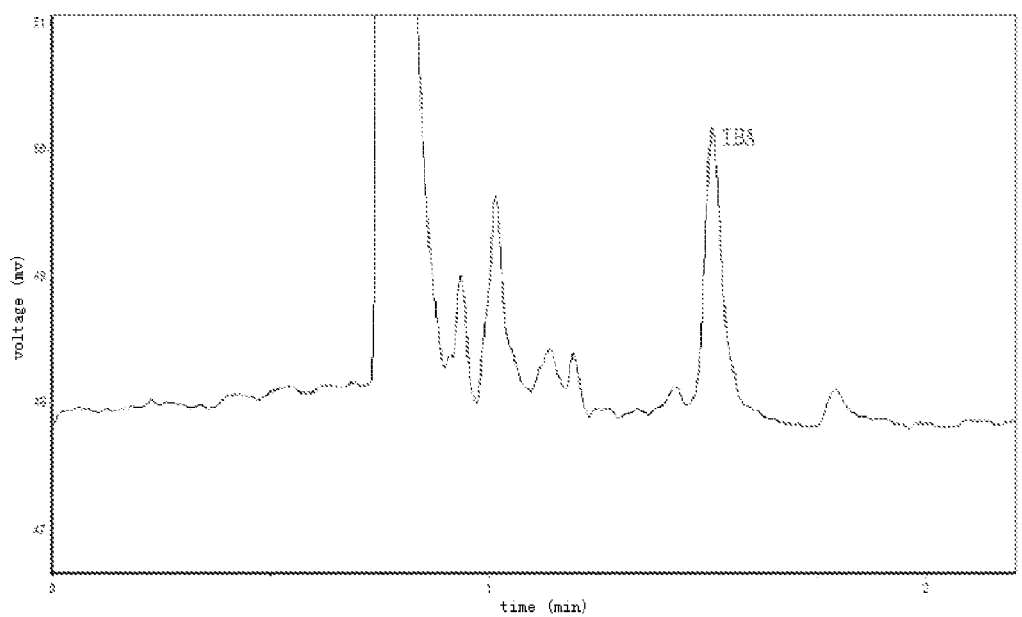

FIG. 4 is the chromatogram of 0.1 μL 2 μg/L tributylamine/aceteone (0.2 pg TBA) obtained by a gas chromatograph coupled with the SID in the present invention. Experimental conditions: the detector temperature is 270° C., the Mo wire temperature is 370-380° C.; 150 mL/min of air supplies as the makeup gas; the injector temperature is 260° C.; the oven temperature is isothermally 140° C. The chromatographic column is 30 mm×0.53 mm i.d.×1 μm SE54 column; 8 mL/min of nitrogen in the constant mode supplies as the carrier gas; splitless injection is used.

DETAILED DESCRIPTION OF THE EMBODIMENT

A surface ionization detector (SID) comprises a metal emitter, a heating rod, a collecting electrode, a reducing liner, a housing, and so on.

The heating rod is mounted on the top cap of the housing, whose outer wall is surrounded by the metal emitter. The collecting electrode is cylindrical, and its lower part is placed in the liner, which is placed in the housing. The bottom of the housing is open. The emitter, the heating rod, the collecting electrode, and the liner are kept coaxial. The collecting electrode is electrically connected with an external micro-current amplifier by a lead passing through the housing.

The metal emitter can be made of molybdenum, platinum, iridium, rhodium or their alloys; often times relatively cheap molybdenum or platinum are adopted. The shape of the metal emitter can be cylindrical or spiral wire. If it is cylindrical, the surface of the cylinder can be thinly grooved into screw thread or gridding to increase the surface area. The surface area of metal emitter is relatively large, and the sensitivity of the detector is relatively high. Polarization voltage of +50~400 V is directly applied on the metal emitter, and a weak positive electric field is formed between the metal emitter and the collecting electrode to collect the positive ions produced by the ionization of samples on the metal emitter surface. In this case, the metal emitter is the polarization electrode at the same time, without another setting of polarization electrode, simplifying the structure of the detector.

The heating rod heats and supports the metal emitter. The shell of the rod is made of quartz, which is high temperature resistant, insulating, and chemically inert, avoiding the adsorption of amines.

The collecting electrode, which is made of conductive materials, such as stainless steel, is used to capture positive ions signals produced by ionization on the metal emitter surface.

The outer diameter of the heating rod is 0.8~5 mm, the inner diameter of the collecting electrode is 1~2 mm bigger than the outer diameter of the heating rod. Thus, the detection cell is less than 600 μL, which can be used as a detector for capillary column or packed column gas chromatograph.

The lower end of the reducing liner is a conduit with a reducing inner diameter, guiding the gas flow and preventing the back diffusion of samples. The reducing liner is made of inert quartz or glass after inert surface treatment to avoid the adsorption of amines. The inner diameter of the upper end of the reducing liner is 0.1~1 mm larger than the outer diameter of the lower end of collecting electrode, muff-coupled with the collecting electrode. The diameter of the inner orifice in the lower end of the liner ranges from 0.5~2 mm, with a length of 10~40 mm, where a capillary column can be inserted and remains a certain interval for the makeup gas to flow into the liner.

The bottom of the housing is open, which comprises an adapter for packed column or capillary column. The adapter for capillary column has a capillary in its center.

The housing is placed in a heated zone. During operation, the whole detector is kept at a setting temperature (150~400° C.). Thus, the temperature of the collecting electrode is close to the setting temperature of the detector, reducing adsorption of amines dramatically.

After the detector is heated to the setting temperature (150~480° C.), a proper voltage (or current) is applied on the heating filament in the heating rod to heat the metal emitter to 300~500° C. After the samples enter the detector, they are carried by the makeup gas to pass through the reducing liner, collide with the hot metal emitter, and are surface ionized. The produced positive ions are accelerated by the polarization voltage, and migrate to the collecting electrode to form a current, which is amplified by a micro-current amplifier and outputted as the detection signal.

The detector in the present invention successfully solves the problem of adsorption of trace amines. The MDA to tertiary amines is $10^{-14}$ g, which is 2~4 orders of magnitudes smaller than the SID commercialized by Shimadzu.

We claim:

1. A surface ionization detector, said detector comprising: a metal emitter, a heating rod, a collecting electrode, a reducing liner, and a housing, wherein said metal emitter is disposed about the outer surface of said heating rod; wherein said reducing liner is adapted to receive a portion of said collecting electrode; wherein said housing is adapted to receive said reducing liner; wherein said metal emitter, said heating rod, said collecting electrode, said reducing liner are coaxial when assembled; and wherein said collecting electrode is electrically connected to an external power source, wherein said reducing liner is made of quartz or inert glass and serves as a conduit for a sample gas.

2. The surface ionization detector according to claim 1, wherein said metal emitter comprises one or more metals chosen from molybdenum, platinum, iridium, rhodium, or alloys thereof.

3. The surface ionization detector according to claim 1, wherein said heating rod comprises a resistive heating element.

4. The surface ionization detector according to claim 1, wherein the body of said heating rod is made of quartz.

5. The surface ionization detector according to claim 1, wherein said collecting electrode is made of conductive materials and said collecting electrode receives the positive ions emitted from said metal emitter.

6. The surface ionization detector according to claim 1, wherein said heating rod is cylindrical in shape and the outer diameter of said heating rod is 0.8-5 mm; and wherein said collecting electrode is cylindrical in shape and the inner diameter of said collecting electrode is larger than the outer diameter of said heating rod by 1-2 mm.

7. The surface ionization detector according to claim 1, wherein a portion of said reducing liner has a tampered inner diameter.

8. The surface ionization detector according to claim 1, wherein said housing has an opening that receives an adaptor from a chromatograph column.

9. The surface ionization detector according to claim 1, wherein said housing is configured to be placed in a heated zone.

10. The surface ionization detector according to claim 1, wherein said metal emitter is connected to an external power source through a lead wire so that the metal emitter is configured to receive a polarization voltage of +50 V to +400 V.

11. The surface ionization detector according to claim 1, wherein said reducing liner has an orifice having a diameter of 0.5-2 mm and a length of 10-40 mm.

12. The surface ionization detector according to claim 1, wherein said metal emitter is in a form of a cylinder or a wire spiral.

13. The surface ionization detector according to claim 12, wherein said metal emitter is cylindrical in shape, wherein an outer surface of the metal emitter is grooved or otherwise roughened to increase its surface area.

* * * * *